United States Patent
Galea et al.

(10) Patent No.: US 10,137,004 B2
(45) Date of Patent: Nov. 27, 2018

(54) INSERTION TOOLS AND METHODS FOR MINIMALLY INVASIVE SPINAL FUSION CAGE

(71) Applicant: Vivonics, Inc., Bedford, MA (US)

(72) Inventors: Anna M. Galea, Stow, MA (US); Eric Klem, Lexington, MA (US); Brendan LaBrecque, Peabody, MA (US)

(73) Assignee: Vivonics, Inc., Bedford, MA (US)

( * ) Notice: Subject to any disclaimer, the term of this patent is extended or adjusted under 35 U.S.C. 154(b) by 155 days.

(21) Appl. No.: 14/190,633

(22) Filed: Feb. 26, 2014

(65) Prior Publication Data

US 2014/0243983 A1   Aug. 28, 2014

Related U.S. Application Data

(60) Provisional application No. 61/770,029, filed on Feb. 27, 2013.

(51) Int. Cl.
| | |
|---|---|
| *A61F 2/46* | (2006.01) |
| *A61F 2/44* | (2006.01) |
| *A61B 17/02* | (2006.01) |
| *A61F 2/30* | (2006.01) |

(52) U.S. Cl.
CPC .......... *A61F 2/4455* (2013.01); *A61F 2/4611* (2013.01); *A61B 2017/0256* (2013.01); *A61F 2002/3052* (2013.01); *A61F 2002/30224* (2013.01); *A61F 2002/30462* (2013.01); *A61F 2002/30471* (2013.01); *A61F 2002/4485* (2013.01); *A61F 2002/4619* (2013.01); *A61F 2002/4627* (2013.01)

(58) Field of Classification Search
CPC ........ A61F 2/44; A61F 2/4455; A61F 2/4611; A61F 2002/30571; A61F 2002/30224; A61F 2002/30462; A61F 2002/4627; A61F 2002/4485; A61F 2002/4619; A61F 2002/3052
USPC ............................................ 623/17.11, 17.16
See application file for complete search history.

(56) References Cited

U.S. PATENT DOCUMENTS

| | | | | |
|---|---|---|---|---|
| 5,171,247 | A * | 12/1992 | Hughett et al. | ............... 606/142 |
| 5,772,661 | A * | 6/1998 | Michelson | ........... A61B 17/025 606/279 |
| 5,810,848 | A * | 9/1998 | Hayhurst | ............... A61B 17/04 606/144 |
| 5,848,437 | A * | 12/1998 | Korst | ..................... G11B 20/12 711/157 |
| 6,387,130 | B1 * | 5/2002 | Stone | ..................... A61F 2/4455 623/17.16 |

(Continued)

*Primary Examiner* — Jacqueline Johanas
*Assistant Examiner* — Tessa Matthews
(74) *Attorney, Agent, or Firm* — Iandiorio Teska & Coleman, LLP

(57) ABSTRACT

An intervertebral support insertion tool includes a tube having a distal open end for insertion in a patient proximate vertebra and a proximal open end. A shaft is received in the tube proximal open end and has a distal intervertebral support interface for engaging an intervertebral support loaded into the tube. A housing supports the tube and shaft with a first drive mechanism such a linear actuator advances the shaft in the tube. A second drive mechanism such as a rotational drive rotates the shaft. In this way the shaft advances and rotates the intervertebral support to position and deploy it between adjacent vertebrae.

28 Claims, 16 Drawing Sheets

(56) References Cited

U.S. PATENT DOCUMENTS

| | | | |
|---|---|---|---|
| 7,905,920 B2 | 3/2011 | Galea | |
| 2007/0276406 A1* | 11/2007 | Mahoney et al. | 606/106 |
| 2009/0043282 A1* | 2/2009 | Hughes et al. | 604/518 |
| 2010/0211119 A1* | 8/2010 | Refai et al. | 606/86 A |
| 2010/0318092 A1* | 12/2010 | Butler et al. | 606/99 |
| 2011/0009969 A1* | 1/2011 | Puno | A61B 17/1757 623/17.12 |
| 2011/0098758 A1* | 4/2011 | Stoy et al. | 606/86 A |
| 2012/0197299 A1* | 8/2012 | Fabian, Jr. | 606/279 |
| 2014/0114334 A1* | 4/2014 | Olson et al. | 606/169 |
| 2014/0257313 A1* | 9/2014 | Frey | A61F 2/4611 606/90 |

* cited by examiner

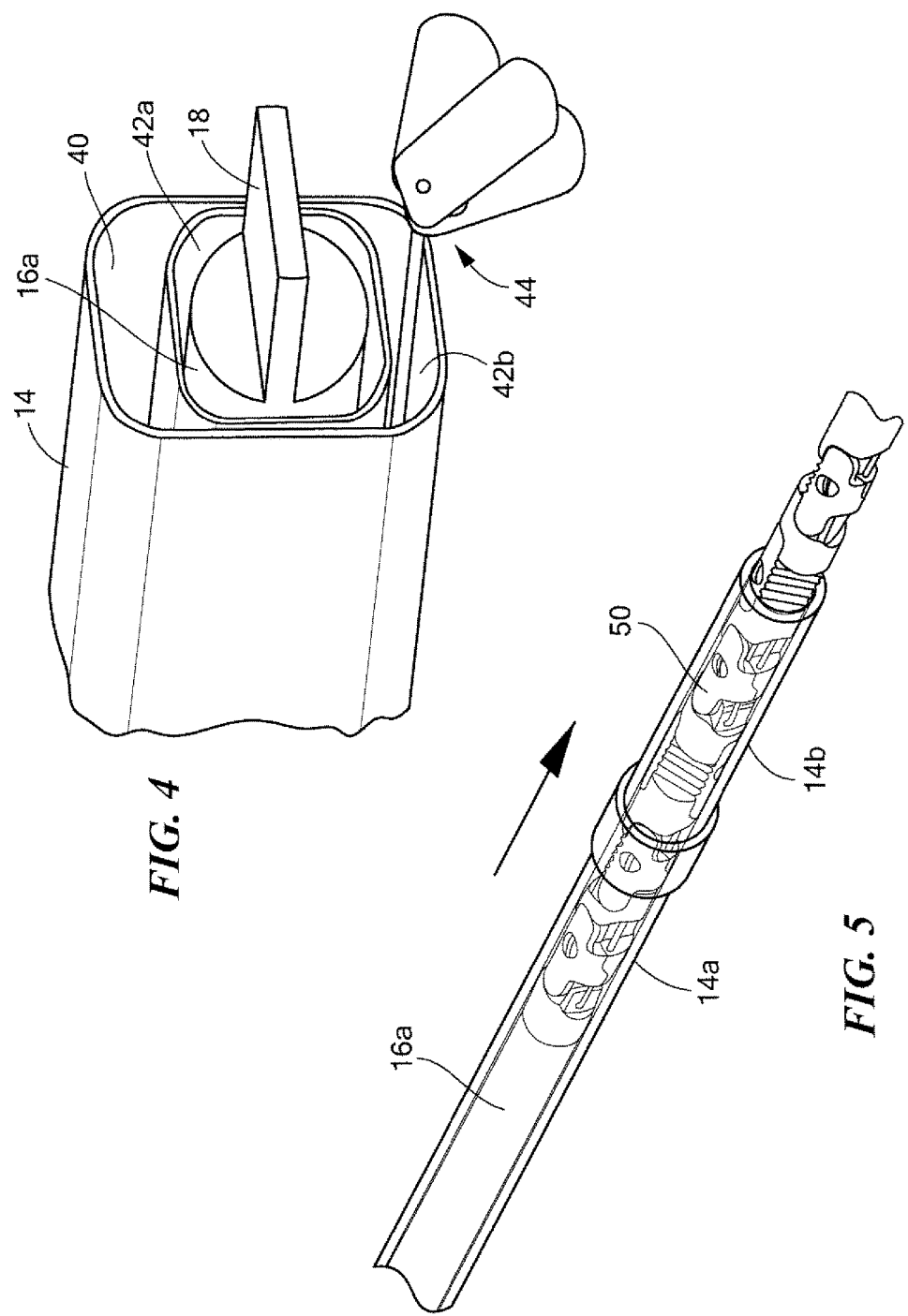

INSERTION TOOLS AND METHODS FOR MINIMALLY INVASIVE SPINAL FUSION CAGE

RELATED APPLICATIONS

This application claims benefit of and priority to U.S. Provisional Application Ser. No. 61/770,029 filed Feb. 27, 2013 under 35 U.S.C. §§ 119, 120, 363, 365, and 37 C.F.R. § 1.55 and § 1.78 and is incorporated herein by this reference.

FIELD OF THE INVENTION

This invention relates to insertion tools and methods for a minimally invasive spinal fusion cage.

BACKGROUND OF THE INVENTION

U.S. Pat. No. 7,905,920, incorporated herein by this reference, discloses a spinal fusion cage in the form of an intervertebral fusion support which is loaded in an access device. For delivery to the space between adjacent vertebrae, the members of the intervertebral fusion support are co-linear. The individual members then rotate and pivot into position forming an intervertebral fusion support (fusion cage) between adjacent vertebrae.

One or more strings or wires may be used to deploy the individual members in the space between adjacent vertebrae.

Insertion and deployment of the intervertebral fusion support members is currently a manual operation.

SUMMARY OF THE INVENTION

The invention features a tool for at least partially automating the insertion and deployment of an intervertebral fusion support to assist the surgeon and to render insertion and deployment possible through minimally invasive techniques. The tool may include one or more of the following features: a device to distract or dilate adjacent vertebrae; to insert a minimally invasive spinal fusion cage; to re-orientate the cage as needed as it is inserted; to insert the cage in discrete steps; and/or to pull on a deployment cable or wire attached to the cage including fastening this deployment cable or wire.

Also featured is compatibility with an entry space into the body of about 5 mm in diameter or greater; compatibility with being used by hand; and compatibility with being made in such a manner that the tool can be sterilized and reused. A device or clamp on the wire can be used to cinch draw wire for cage final position. One tool assists in the applying or binding the cinching clamp. One cannula can be designed to safely store a cage within and packaged in a sterile pouch. In operating room (OR), this assembly is unpackaged and mounted to the sterile reusable insertion tool front and a deployment wire end may be assembled to the tool feature. A multiple part cannula provides a pathway for the insertion of the implantable device but may be disassembled once the implantable has reached a semi or partially deployed state. During surgery, this cannula would interface with another cannula which is mounted to the patient previously. Connection of the cage to the device head and a special wire connection that can be disassembled via the release of wire tension is also featured.

Featured is an intervertebral support insertion tool comprising a tube having a distal open end for insertion in a patient proximate vertebrae and a proximal open end. A shaft is received in the tube proximal open end and has a distal intervertebral support interface for engaging an intervertebral support which may be loaded into the tube. A housing supports the tube and shaft. A first drive mechanism advances the shaft in the tube and a second drive mechanism rotates the shaft. The tube may include two cannula sections. The shaft may include a main shaft and an interface shaft.

The tube distal end may, in one embodiment, be shaped so the tube distal end can be inserted between adjacent vertebrae to distract the vertebrae. In one version, the tube distal end has a cross section which is not round. Also, there may be a clearance between the tube and the shaft for the insertion of one or more additional instruments in the tube with the shaft.

In one embodiment, the first drive mechanism may include a rack attached to the shaft and a gear mounted to the housing driving the rack to advance the shaft. The tool may include a handle for rotating the gear. In one embodiment, the second drive mechanism includes a cam follower attached to the shaft and the housing or a cannula section may include a groove driving the cam follower and configured to rotate the shaft.

The tool shaft may include a bearing between first and second sections thereof allowing the second section to rotate via the second drive mechanism and the first section to be advanced by the first drive mechanism. The tool tube may also have first and second sections, e.g., a first section fixed to the housing and a second disposable section attached to the first section and including the distal end of the tube.

The tool may further include a tensioner mechanism such as a cam shaped spool mechanism on the housing for pulling a wire associated with the intervertebral support. The spool mechanism may be rotated by a handle on the housing.

Also featured is an intervertebral cage insertion tool comprising a housing with a cannula for an intervertebral cage loadable therein, a shaft received in the cannula having a cage interface for engaging a cage loaded in the cannula, a linear actuator configured to advance the shaft in the cannula in a step wise fashion to advance the cage, and a rotational drive configured to rotate the shaft in step wise fashion to deploy the cage.

The linear actuator may include a rack attached to the shaft and a gear mounted to the housing driving the rack to advance the shaft. The rotational drive may include a cam follower on the shaft guided by one or more housing features. Other linear actuators and rotational driver may be used.

One intervertebral support insertion tool includes means for advancing a shaft in a tube to advance the intervertebral support and for rotating the shaft in the tube to deploy the intervertebral support. In one design, the means for advancing the shaft in the tube and for rotating the shaft in the tube includes a rack attached to the shaft and a gear driving the rack to advance the shaft and a cam follower attached to the shaft configured to rotate the shaft.

A method of inserting and deploying an intervertebral support includes activating a mechanism and, in response to activation of the mechanism, automatically advancing and/or rotating the intervertebral support and/or automatically tensioning a wire associated with the intervertebral support to deploy the intervertebral support between adjacent vertebrae.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features, and advantages will occur to those skilled in the art from the following description of a preferred embodiment and the accompanying drawings, in which:

FIG. 4 is a schematic view of the distal end of the tube or cannula portion of the tool of FIG. 1;

FIG. 5 is a schematic view showing two tube sections with an intervertebral support loaded therein and being pushed and turned by the tool shaft of in FIG. 1;

DETAILED DESCRIPTION OF THE INVENTION

Figure 1:
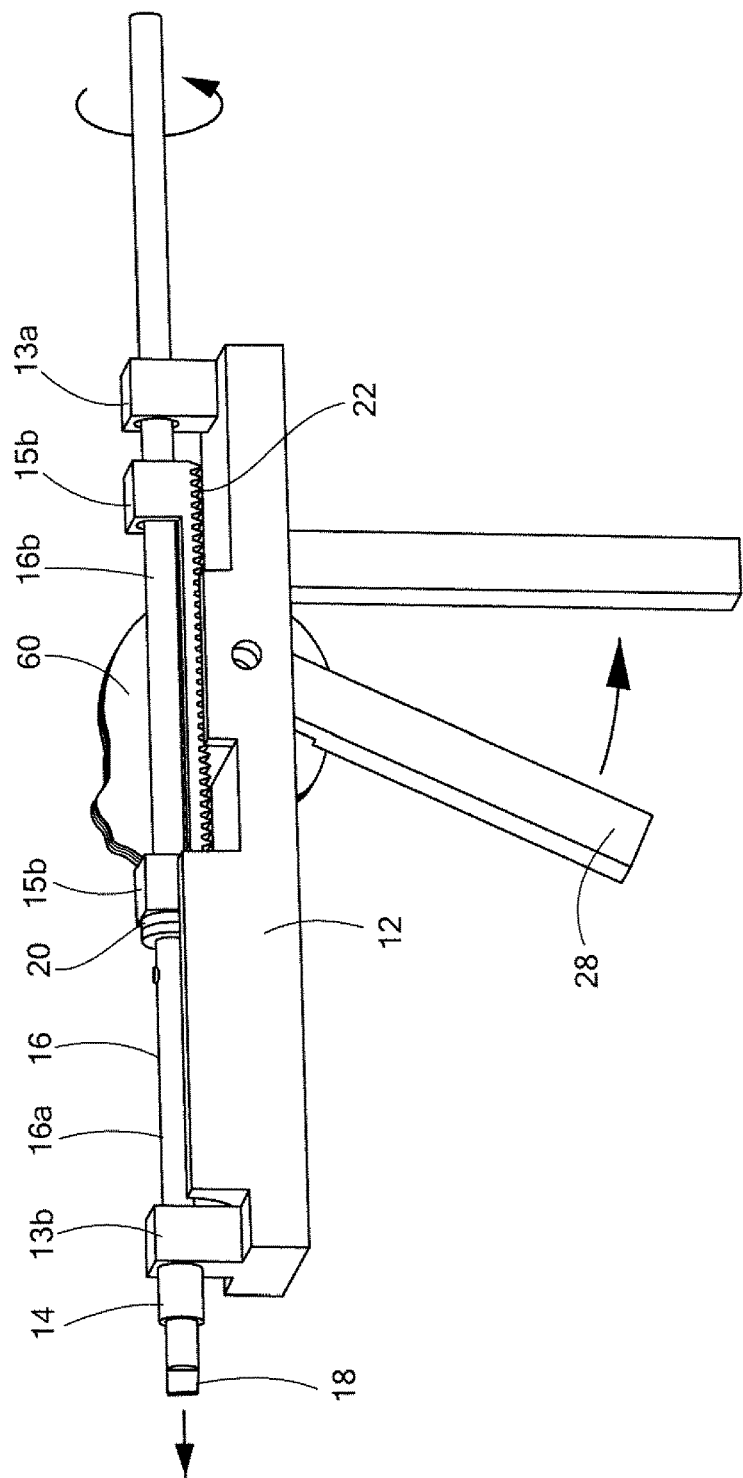
FIG. 1 is a schematic front view showing an intervertebral support insertion tool in accordance with one example of the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows an example of intervertebral support tool 10 with housing 12 supporting tube or cannula 14 (which may be in two or more sections) and which is preferably no greater than 5-8 mm in diameter. The tube has an open distal end and an open proximal end and defines a lumen for loading an intervertebral support therein (such as shown in U.S. Pat. No. 7,905,920) when all the members thereof are co-linear.

Shaft 16 enters the proximal open end of tube 14 and includes a distal intervertebral support interface at 18 for engaging the intervertebral support at its proximal end. Here, shaft end 18 is formed as a blade and a proximal intervertebral support member (for example a cross member or a support member) would have a corresponding slot receiving this blade so that as shaft 16 rotates it also rotates the intervertebral support members in order to deploy the intervertebral support cage into the space between adjacent vertebrae. Other interfaces between the shaft and intervertebral support cage include other mechanical interfaces, magnetic interfaces, friction fits, or other methods which allow force and torque to be transmitted from the shaft to the cage. In one embodiment, the interface also enables the cage to be pulled as well as pushed and therefore the cage could retained to the shaft in a releasable fashion with a mechanism such as a locking detent.

There are means for advancing the shaft in the tube to push and deliver to the site the intervertebral support cage and for rotating the shaft to rotate the intervertebral support cage to deploy it in the site between adjacent vertebrae. Preferably, the shaft advances in a step wise fashion but each advancement step need not be the same. Each step may be between 2 and 15 mm. The shaft is also preferably rotated in a step wise fashion. In one example, the shaft and thus the intervertebral support members loaded into the tube rotate clockwise x° in one step, rotate another y° clockwise in the next step, and then rotate counter clockwise back x°+y° in another step and then repeat this step wise rotation sequence until the intervertebral support cage is fully inserted and deployed between adjacent vertebrae. Other rotation sequences are possible.

Figure 2:
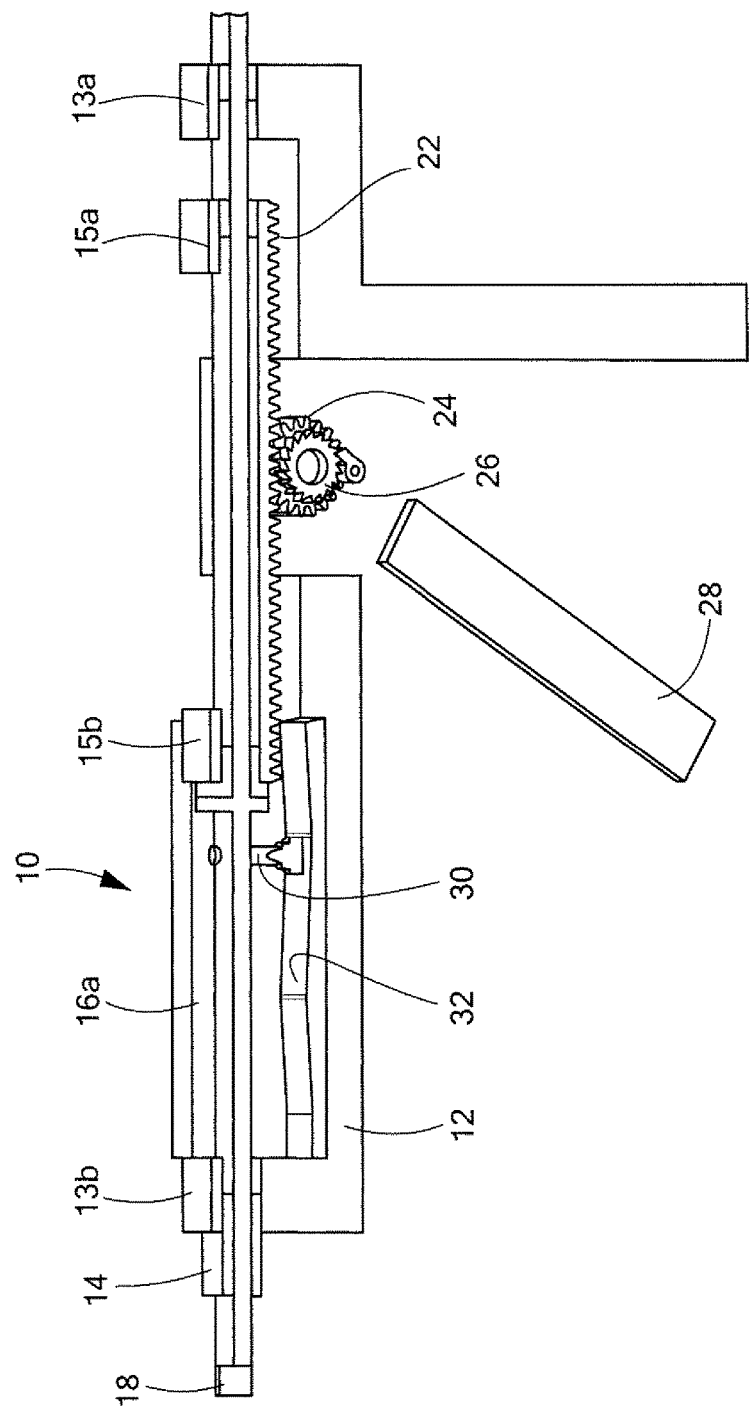
FIG. 2 is another schematic view of the tool of FIG. 1 with portions of the housing removed for clarity.

In one example, linear advancement of the shaft and intervertebral support is effected by a first drive mechanism such as a linear actuator. In one design, shaft 16 includes two sections 16a and 16b coupled by a bearing such as thrust bearing 20 so shaft section 16a can rotate relative to shaft section 16b. The shaft sections in this design are supported by housing supports 13a and 13b and the tube. Rack 22 is coupled to shaft section 16b as shown via bushings 15a and 15b and rack 22 is driven by pinion gear 24, FIG. 2 rotated by ratchet mechanism 26 and handle 28. Each pull of handle 28 may advance shaft 16 a predetermined small distance to insert and deploy the intervertebral support cage. The ratchet mechanism shown serves to further the travel distance of the rack so that multiple strokes of the grip can be taken. It also serves to prevent an accidental occurrence of retracting the spinal cage in the middle of the procedure.

Figure 3:
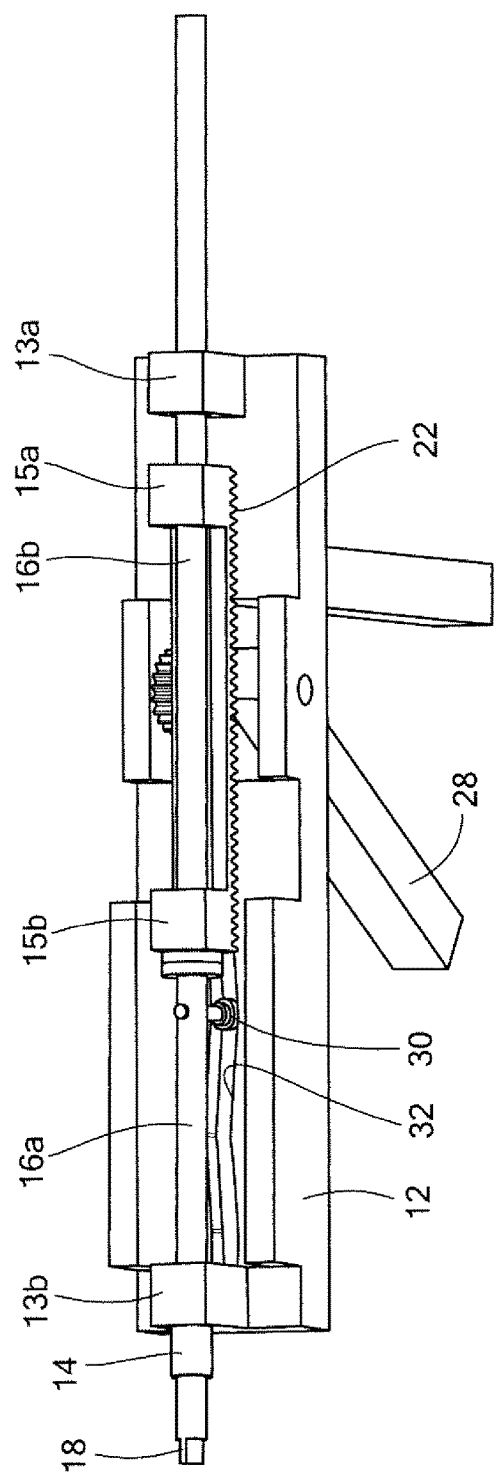
FIG. 3 is a schematic top view of the tool shown in FIG. 1.

To rotate shaft section 16a and thus the intervertebral support to deploy it, shaft section 16a has, in this design, cam follower 30, FIG. 3 and housing 12 includes adjacent groove profile 32 configured to cause the shaft to rotate as cam follower 30 moves within or in an abutting relationship with groove 32 or a rail or other feature to cause the shaft to rotate preferably in a stepwise fashion described above.

Other means for linearly advancing the shaft and for rotating the shaft include other linear actuators including a motorized device. Screw threads on the shaft may also be used to rotate it. It is preferred that the shaft is free to rotate and also to move around within the tool to allow for the motions necessary for deployment of the cage. Passive turning or lateral motion may be allowed by allowing the shaft to rotate or move with the intervertebral support cage or by allowing the cage to rotate relative to the shaft at the interface between the two. The cage may be inserted in one long motion or may be inserted in multiple discreet motions each with its own forward motion and potentially rotational and transverse motions. In the rack and pinion embodiment shown, each pull of the handle advances the shaft by a distance set by the teeth on the rack. The teeth on the rack and pinion may be set such that the distance traveled varies with each pull as desired. Alternately, another device such as a shaped rack can generate the same effect. A sheer pin may be implemented with the handle to ensure that the cage is not forced into a space where it or the anatomy may be in danger of breaking.

The distal end 40 of tube or cannula 14, FIG. 4 may have a non-circular cross section (e.g., rectangular as shown) to assist in distracting the intervertebral space. The vertebrae disk to be removed can be done so with standard conventional tools. Once the tool of FIG. 1 is brought in close proximity to the disk space, the space may need to be distracted or opened further to provide extra spinal length or to provide extra space that may be needed to deploy the intervertebral support cage. Because the minimally invasive spinal cage may be inserted with interference, the final disk spacing can be less than the insertion spacing so that the disks tightly clamp the cage at all times to prevent movement. Distraction by be accomplished by using a hollow tool tube that has a cross section that is not round. A rectangular cross section is shown in FIG. 4. Square, oval, or one of a number of shapes may be used. In this manner, the hollow tube end can be inserted between the vertebrae, at the edge of the vertebra, or further depending on the application and rotated about its long axis to widen the space. Thus, the tool tube itself may be used to insert and deploy the intervertebral support cage and also to distract adjacent vertebra. Alternatively, or in addition, distraction tools may be inserted which pry, wedge, or fan open the space for the intervertebral cage to be inserted into. These devices may ratchet to their open configuration and then lock in place until insertion is completed at which point they are released and withdrawn. If there is a clearance between the inner diameter of the tube and shaft 16 as shown in FIG. 4, there may then be space to allow for the insertion of other medical instruments as discussed above along with the shaft in the tube. FIG. 4 shows how cannula 14 can include port 42a for the intervertebral support cage and shaft 16a and port 42b for distraction tool 44.

In the design of FIG. 5, the tube is in two sections, 14a and 14b, releasably coupled together. And intervertebral support 50 is also shown loaded into the tube sections as is shaft section 16a. Tube section 14a may be housed via support 13b, FIG. 1 while tube section 14b is removable and optionally disposable or reusable for other surgeries if cleaned and sterilized.

Figure 6:
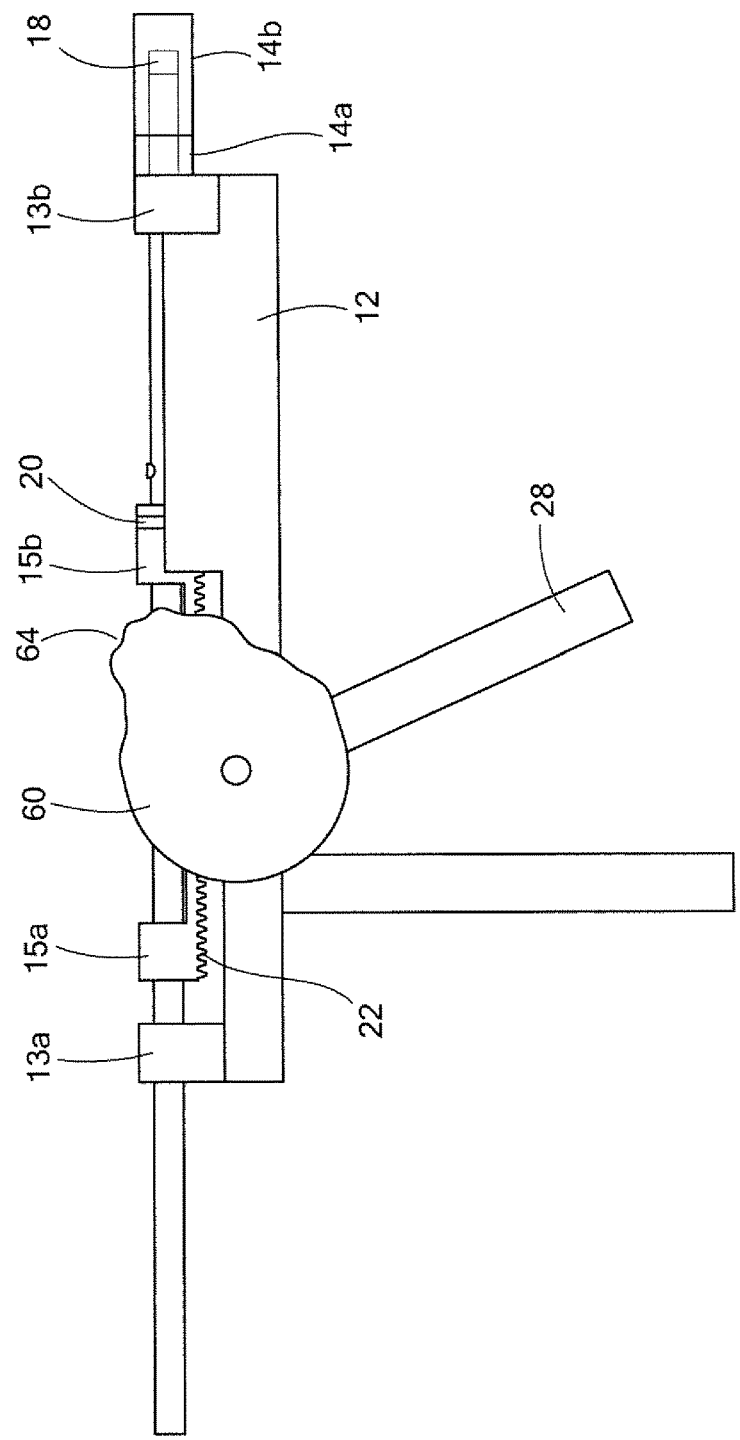
FIG. 6 is a schematic rear view of the tool shown is FIG. 1.

Also featured in one design for intervertebral support configurations with one or more wires or cables is a spool mechanism 60, FIG. 6 configured to rotate with each pull of handle 28 to pull on or tension a wire or wires coupled to the intervertebral support and exiting out of tube 14 and around cam shaped spool 64. Thus, in this design, handle 28 rotates both the spool and the rack drive gear. The stringer wire may be wound on the spool which is synced in such a way that with each pull of the trigger and attendant turn of the spool, a pre-set amount of string is deployed. A non-round cam shaped spool is shown and a spring may be implemented on the cam in order to account for tolerance stackup and give the system compliance. Alternative methods include a spring to apply a constant pressure at all times, a cam drive of a circular pulley, a motor and pulley controlled to take up the correct amount of string, and a separate level actuation system for the string.

The entire mechanism is intended to be reversible so that the spinal cage can be retracted during any part of the procedure prior to releasing the intervertebral support from the interface shaft. One method to reverse the process is to use a second ratchet method which drives the rack in the opposite direction of the first. The distal inner edge of the cannula would encourage the deployed stage intervertebral support portions to undeploy, so that they line up as they were in a loaded state to fit within the inner diameter of the cannula. Incorporating chamfered edges on the end of the cannula can help to ensure that the extraction proceeds smoothly. By securing the end of the tool to the spinal cage or insertion tool, it is ensured that the tool will not retract from the end of the cage.

Figure 7A:
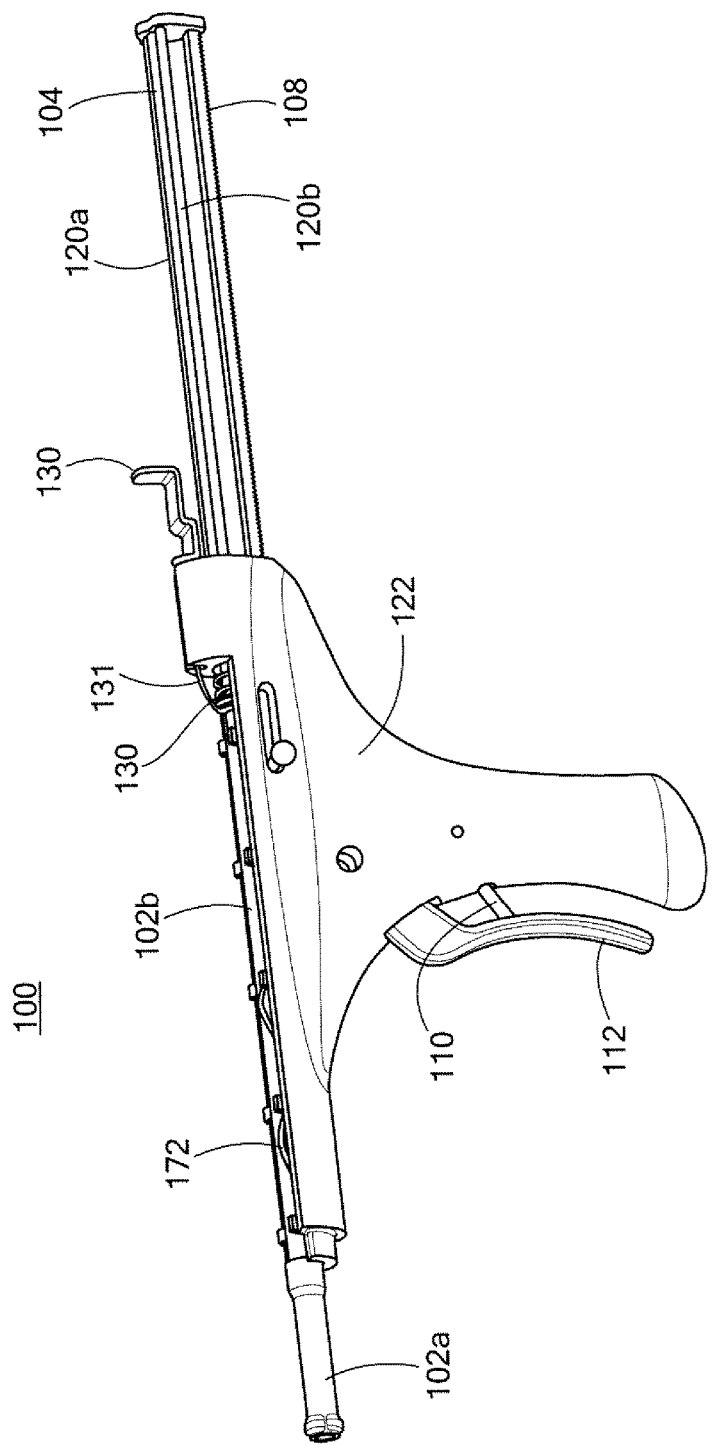
FIGS. 7A-7C are schematic views showing another embodiment of an intervertebral support insertion tool in accordance with examples of the invention.
Figure 7B:
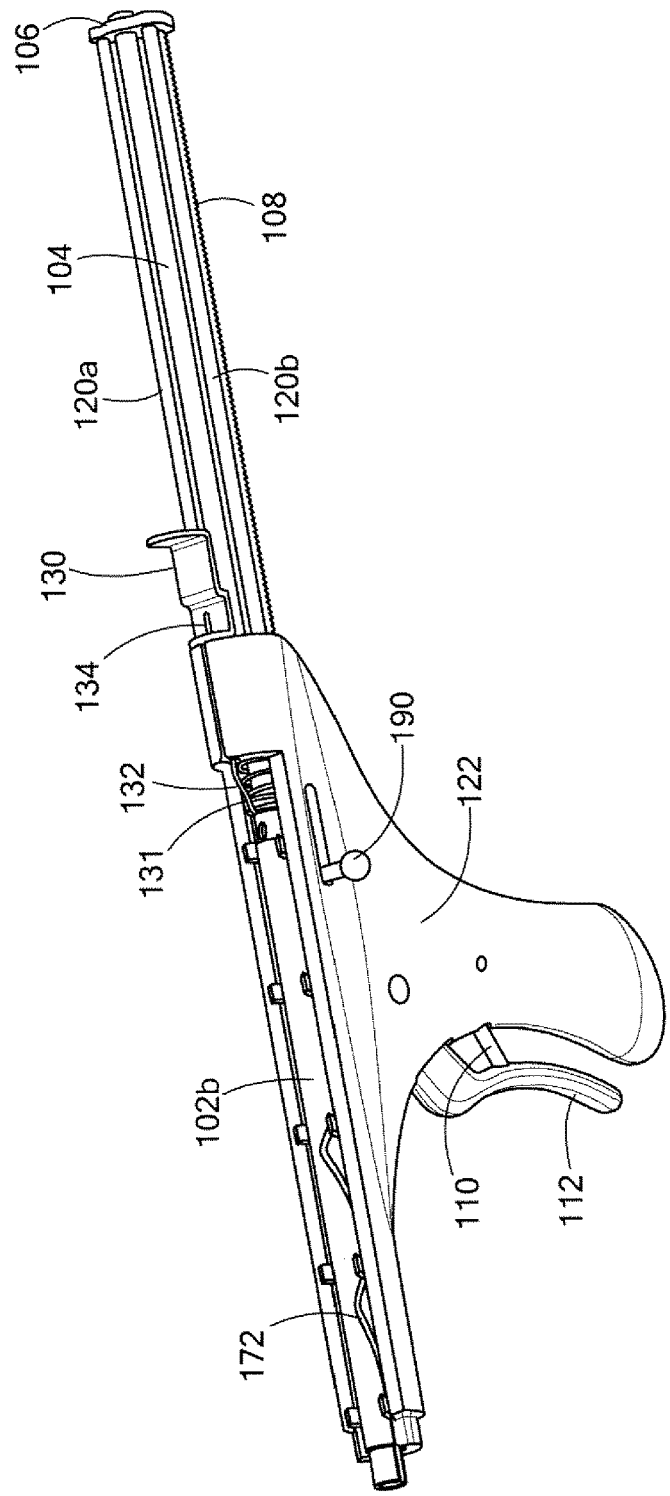
Figure 7C:
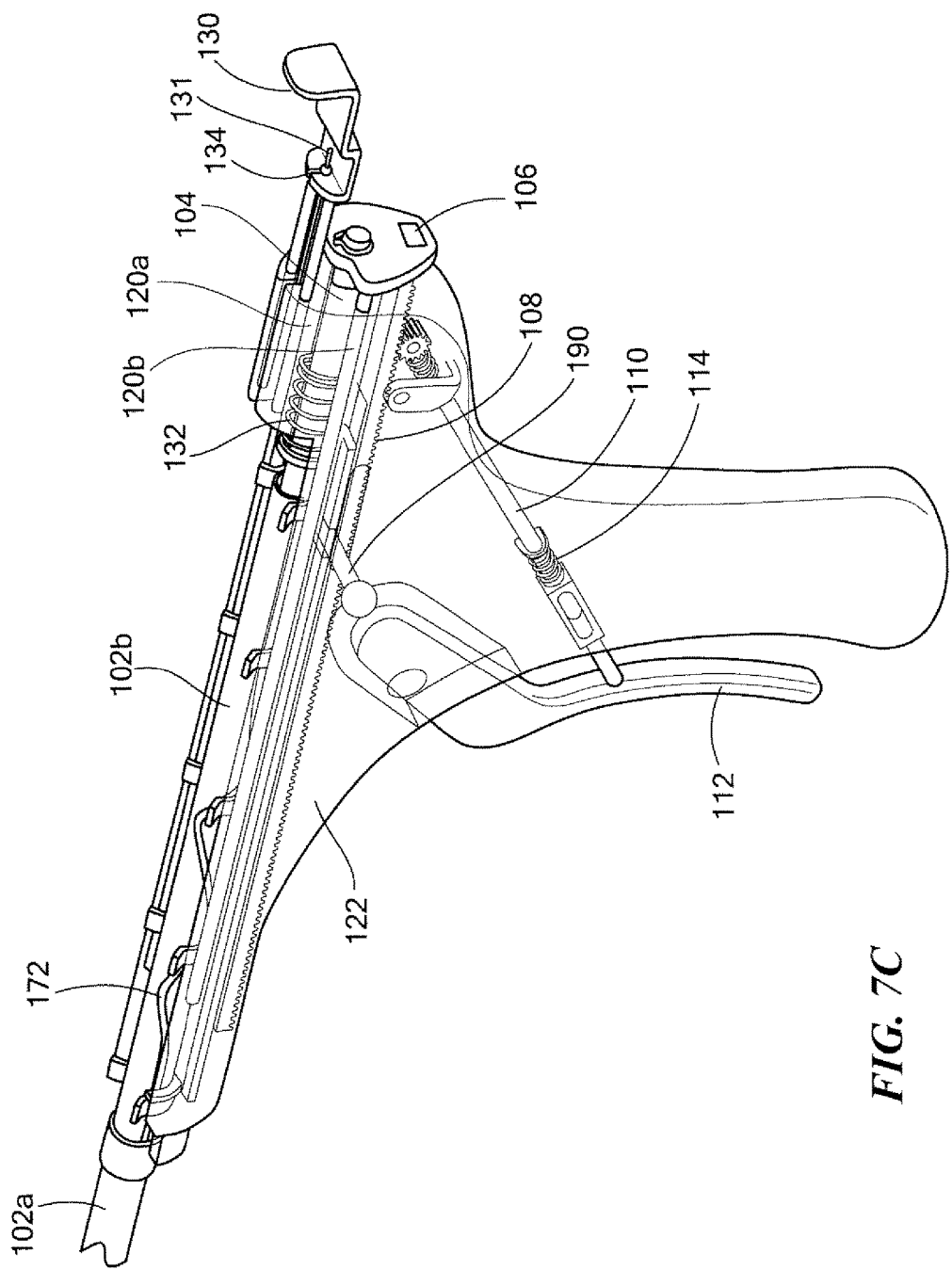

FIGS. 7A-7C show another intervertebral insertion tool 100 typically used in connection with cannula or tube portion 102a and cannula or tube portion 102b. The main shaft 104 advances an interface shaft loaded in cannula 102b and the interface shaft advances and rotates the intervertebral support also loaded in cannula section 102b. Shaft 104 is supported and advanced by but can rotate relative to pusher assembly 106 which includes a rack 108 driven by a pinion rotated by push rod 110 driven by lever 112. Spring 114 serves to return the lever to its actuatable position after each pull of the lever. Guide rails 120a and 120b are received in channels in housing 122.

A mechanism such as tensioner 130 keeps tension on any wire(s) 131 associated with the intervertebral support and is biased rearwardly by spring 132. Wire 131 can be releasably locked in slot 134 of tensioner 130.

Figure 8:
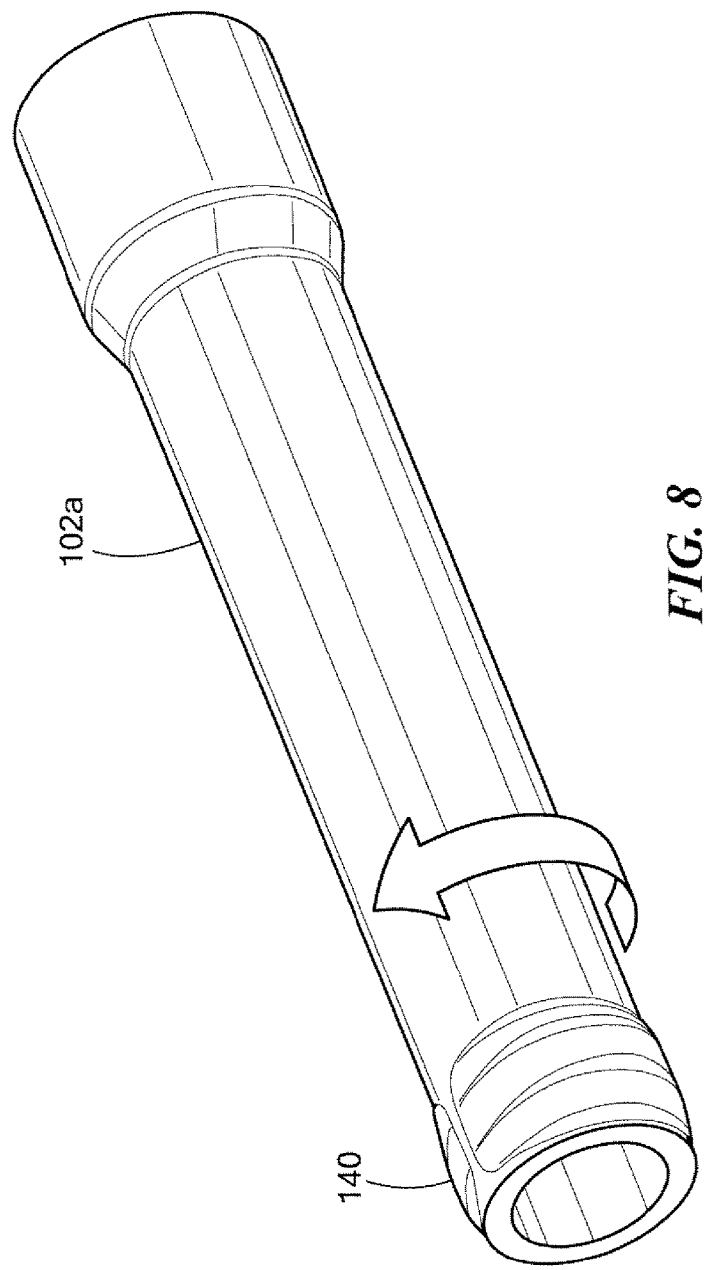
FIG. 8 is a schematic front view showing one cannula portion used with the tool shown in FIG. 7A-7C.

Cannula 102a, FIG. 8 may include a distal cam surface 140 for vertebrae distraction. Interface shaft portion or cage interface 150, FIGS. 9A-9B has a distal end which interfaces with intervertebral support 152 and a proximal end with an interface of the distal end of main shaft 104, FIGS. 7A-7C. Here the main shaft interface is slot 160 and opening 162 leading into slot 160 for hook shaped distal end 164, FIG. 11 of main shaft 104 which is received in detent 160, FIGS. 9A-9B and in opening 162. In this way, retraction of the main shaft also retracts the interface shaft and the cage.

Figures 9A, 9B:
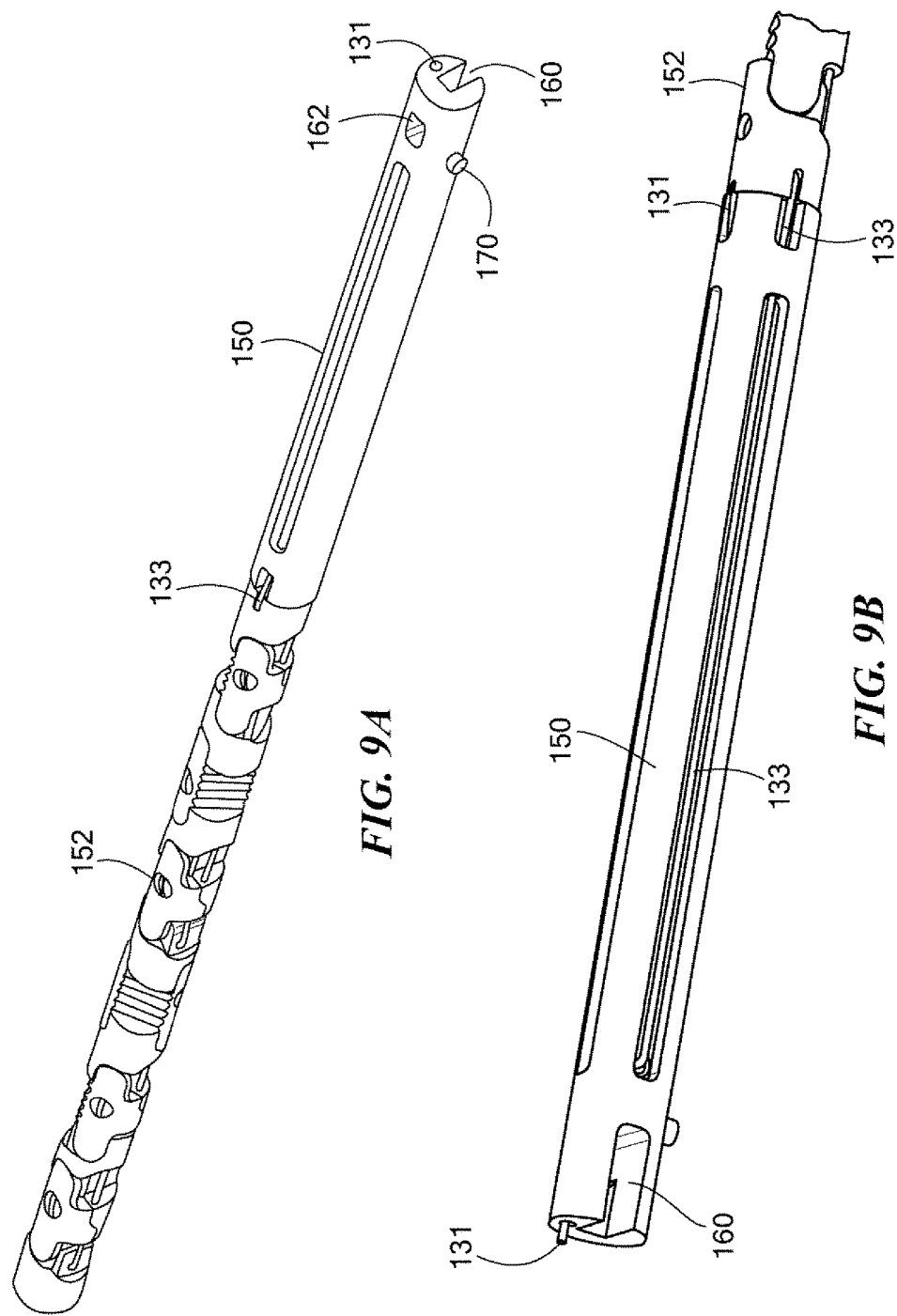
FIGS. 9A-9B are schematic views showing a shaft interface portion used with the tool of FIGS. 7A-7C.
Figure 10:
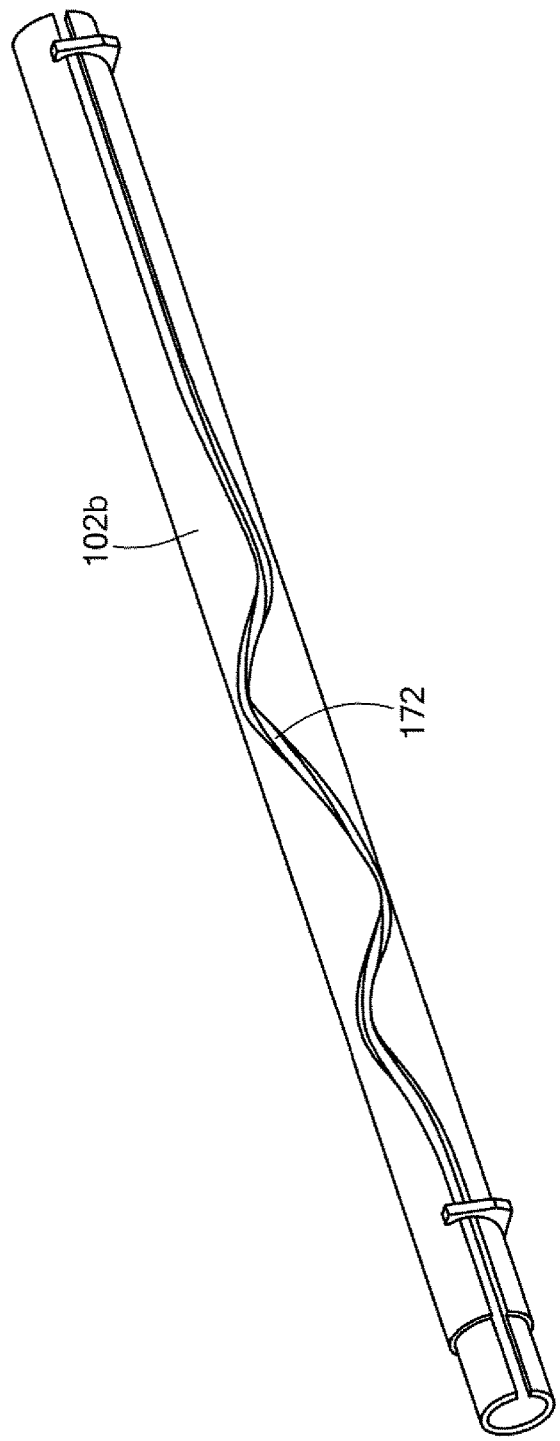
FIG. 10 is a schematic front view showing the other cannula portion loadable into the tool of FIGS. 7A-7C.

Interface shaft 150 also includes follower 170 which is received in groove 172, FIG. 10 of cannula portion 102b to rotate interface shaft 150, FIG. 9 and main shaft 104, FIGS. 7A-7C and FIG. 11. Thus, as main shaft 104 is advanced, so is interface shaft 150 and intervertebral support 152 and interface shaft 150 and main shaft 104 also rotates to rotate intervertebral support 152 inside cannula section 102b, FIG. 10 (and also while inside cannula section 102a, FIG. 7A). Main shaft 104 can also be pulled rearward which withdraws interface 150 and the intervertebral support. Deployment wire 131 passes through the length of interface shaft 150, FIG. 9. The interface component manages the wire during the motions of the surgical procedure, and eventually allows the wire to operate from the proximal end of the cannula once the tool is removed. A second attachment wire 133 wraps the distal end of the interface shaft 150, FIG. 9A to the proximal interface of intervertebral support 152 to join the two together. This attachment wire 133 and the face to face butt connection of 152 and 150 allows push, pull and rotation force manipulations from interface shaft 152 to carry through the intervertebral support 152. The attachment wire 133 wraps back to the proximal end of the interface component, where the wire ends cross over one another, and are fixed in place by a fastening component, such as a set screw accessible via detent or slot 160. The fastening component may be disengaged to free the crossing ends of wire 133, so that the wire may be pulled out entirely to release the intervertebral support 152 from the interface shaft 150. The interface shaft 150 may be a rod the same diameter as the loaded state intervertebral support. At the proximal end of the rod, a connection feature 160 such as a square keyhole is used to transmit linear force and torque. A detent 162, is used to allow the tool to pull the system back out. A wire/cable 133 runs the length of the component and provides a secure attachment to the cage at the distal end.

Figure 11:
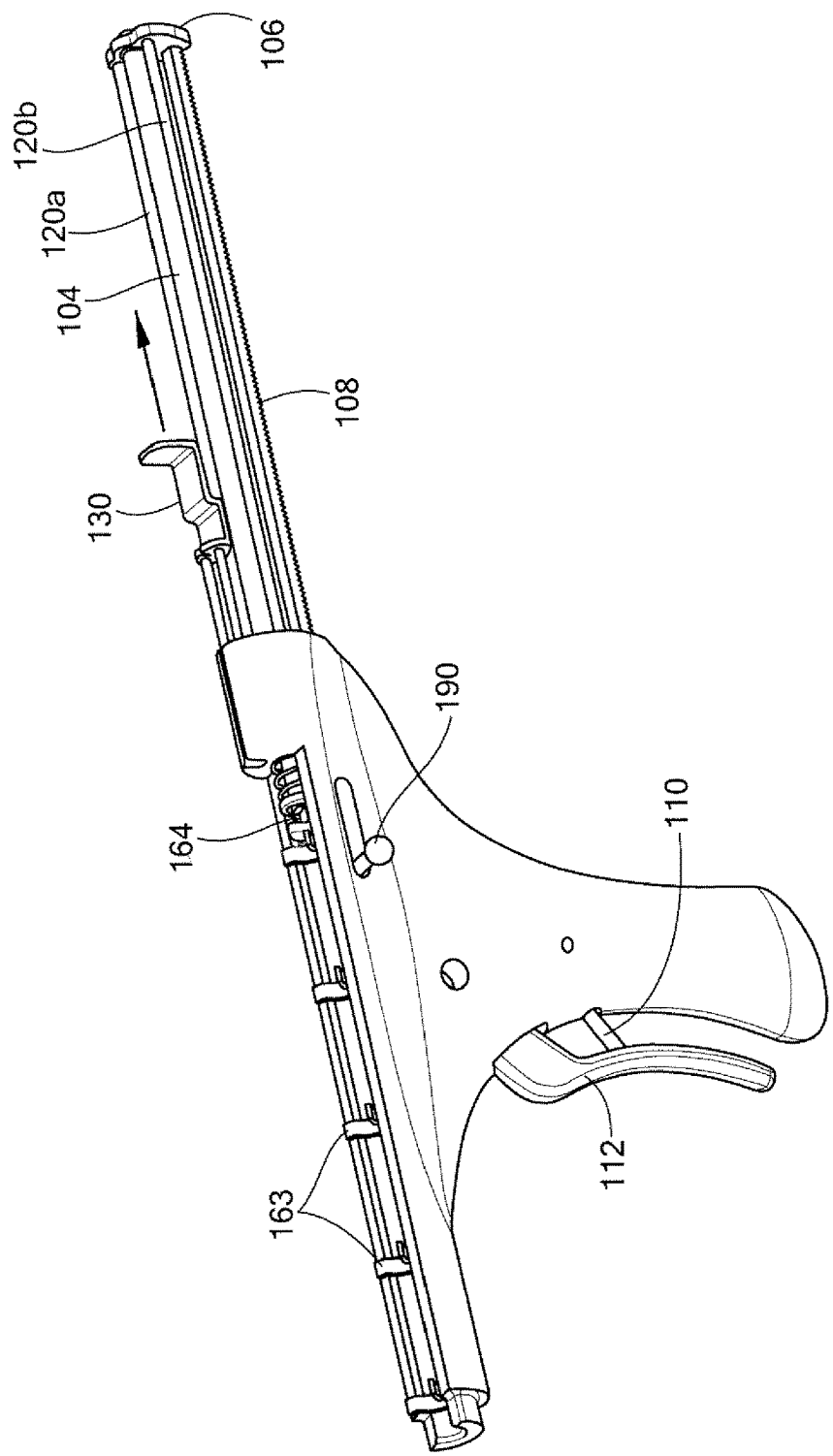
FIG. 11 is a schematic view of the tool of FIGS. 7A-7C without the cannula sections in place.
Figure 12A:
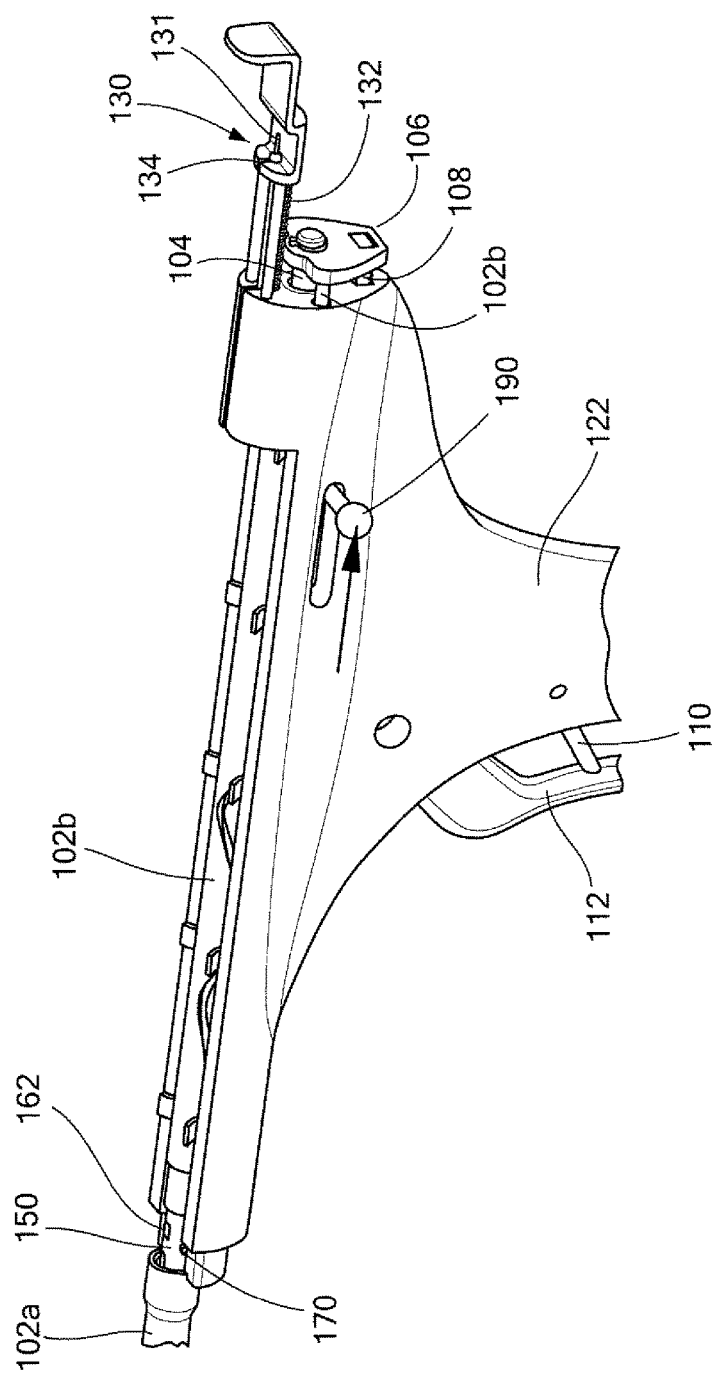
FIGS. 12A-12C are schematic views showing how the intervertebral support can be released from the insertion tool.
Figure 12B:
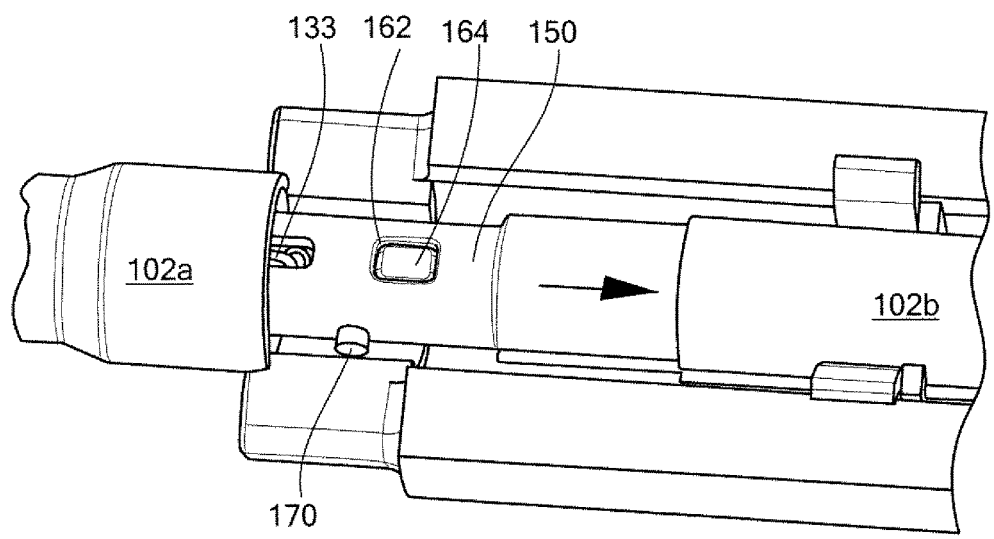
Figure 12C:
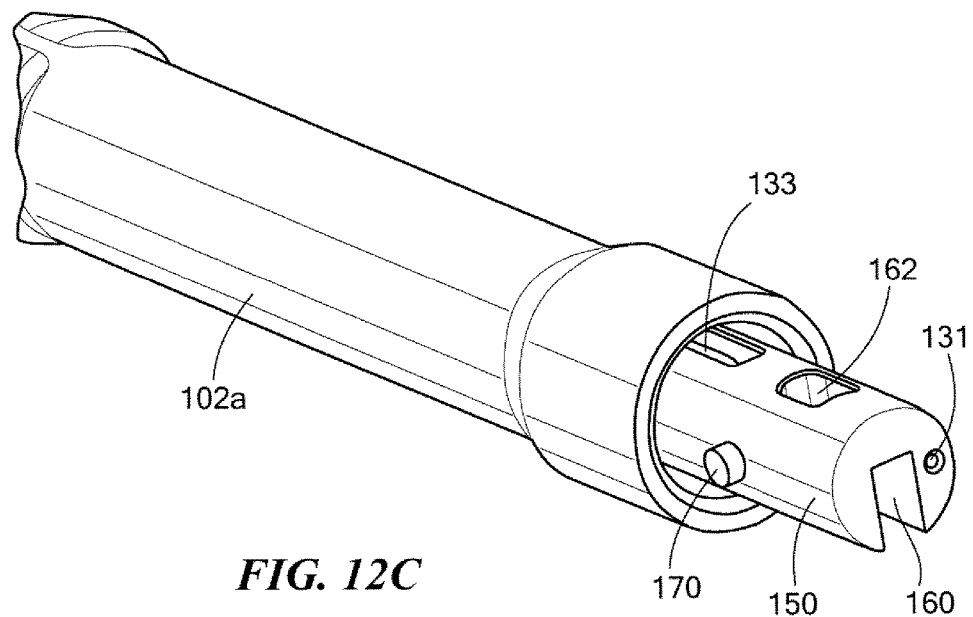

FIG. 11 shows the tool without the cannula or interface shaft or intervertebral support loaded therein. In FIGS. 12A-12B, cannula sections 102a and 102b can be separated by pushing lever 190 rearward. This lever mechanism is coupled with cannula 102b and is normally closed provided by a spring load from a spring. Pulling the lever disassembles the continuity between cannula 102a and cannula 102b, exposing the end of the interface component 150. With the interface component accessible to the user, the wire or other connection mechanism can be detached allowing the intervertebral support and interface component to be separated. In one example, lever 190 is attached to an arm with a distal feature which engages cannula 102b. U-shaped supports or clips 163 are for supporting the cannula 102b and may retract relative to the tool housing.

Figure 13A:
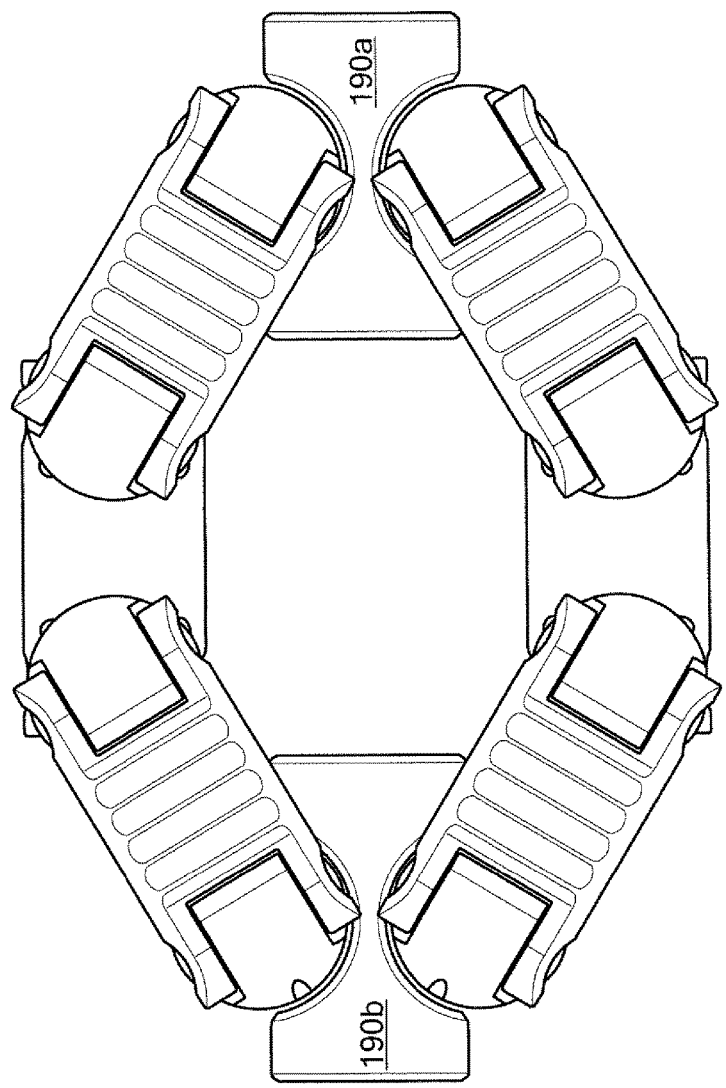
FIGS. 13A-13B are schematic views showing two crescent forming intervertebral supports implanted one after the other using the tool of FIGS. 7A-7C and constrained using connecting components.
Figure 13B:
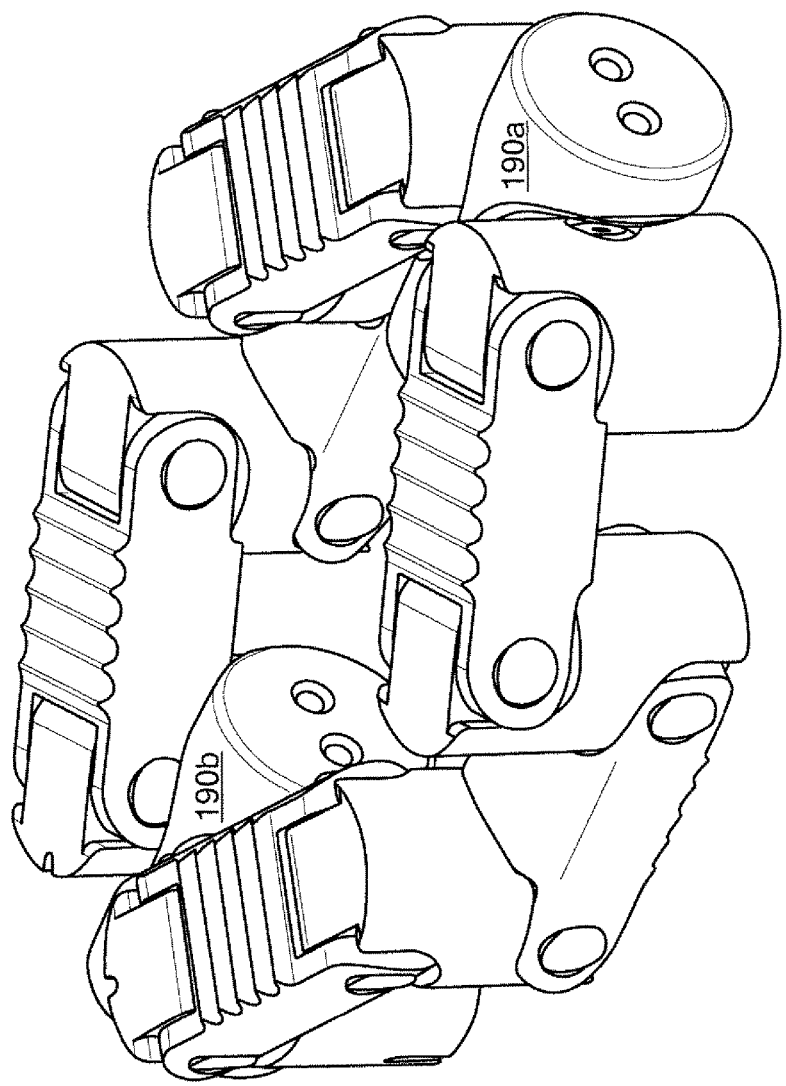

In FIGS. 13A-13B, two intervertebral supports each form a crescent when implanted are constrained via members 190a and 190b. Intervertebral support members may be inserted through the tool and cannula in alternating order are after multiple intervertebral supports are deployed, to connect multiple intervertebral supports to form a single intervertebral support assembly. By using multiple intervertebral supports that are attached together with support members, instead of one continuous intervertebral support, each support may be much shorter allowing for easier deployment. The number of intervertebral support members would likely match the number of intervertebral support assembled. Members 190a and 190b connect these two supports to ensure that they are fully constrained and cannot move out of place or undeploy. The intervertebral support members may contain an external profile that matches the profile of the inside lumen of the cannula. The intervertebral support members may have features or removed material to help affix to the adjoining adjacent intervertebral supports. The intervertebral support members may contain through holes to allow tracking the device down a wire origination from the intervertebral supports, which may have been used to deploy the intervertebral support such as wire 131.

In some embodiments, the two part cannula described contains the spinal cage which is contained in a loaded state taking up minimum clearance required equal to the outside diameter of the cage section. Alternately, the cage can be loaded into the cannula and tool. Also, the shaft interface component described interfaces the spinal cage with appropriate portions of the main shaft and may be contained within cannula portion 102b. The deployment tool may be removed from cannula section 102a after the spinal cage has been inserted into the body. Then, other tools may be inserted down cannula section 102a after spinal implantation has occurred to perform other tasks such as filling the space with bone growth material, finalizing the position and location of the implanted spinal cage, inserting the spinal cage connecting components described above with respect to FIGS. 13A and 13B, or other procedures. To insert a second crescent shaped spinal cage, cannula portion 102a may be left in place in the body between adjacent vertebrae and the second crescent shaped cage can be loaded into the tool and deployed as described above as required to complete the surgery. Then, additional components as described in FIGS. 12A and 12B can be implanted to couple the first and second cages.

In accordance with the methodology described herein, a mechanism such as lever 112, FIG. 7A is actuated and the result is the automatic advancing and rotation of the intervertebral support and also an automatic tensioning of wire(s) associated with the intervertebral support to deploy the intervertebral support between adjacent vertebrae.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. An intervertebral support insertion tool system comprising:
   a tube having a distal open end for insertion in a patient proximate vertebrae and a proximal open end;
   a distal intervertebral support;
   a shaft received in the tube proximal open end and having an interface for engaging the distal intervertebral support loaded inside the tube; and
   a housing supporting the tube and shaft with a first drive mechanism to advance the shaft in the tube and a second drive mechanism to rotate the shaft.

2. The tool of claim 1 in which the tube distal end is shaped so the tube distal end can be inserted between adjacent vertebrae to distract the vertebrae.

3. The tool of claim 2 in which the tube distal end has a cross section which is not round.

4. The tool of claim 1 in which there is clearance between the tube and the shaft for the insertion of one or more additional instruments in the tube with the shaft.

5. The tool of claim 1 in which the first drive mechanism includes a rack attached to the shaft and a gear mounted to the housing driving the rack to advance the shaft.

6. The tool of claim 5 further including a handle for rotating the gear.

7. The tool of claim 1 in which the second drive mechanism includes a cam follower attached to the shaft.

8. The tool of claim 7 further including a groove driving the cam follower and configured to rotate the shaft.

9. The tool of claim 1 in which the shaft includes a bearing between first and second sections of the shaft allowing the second section to rotate via the second drive mechanism and the first section to be advanced by the first drive mechanism.

10. The tool of claim 1 in which the tube has a first cannula section and a second cannula section, the first cannula section supported by the housing and the second cannula section attachable to the first cannula section and including the distal end of the tube.

11. The tool of claim 1 further including a mechanism on the housing for pulling a wire associated with the intervertebral support.

12. The tool of claim 11 in which the mechanism is rotated by a handle on the housing.

13. The tool of claim 11 in which the mechanism is cam shaped.

14. The tool of claim 1 including a main shaft and an interface shaft driven by the main shaft and removably attached to the intervertebral support.

15. The tool of claim 14 in which the interface shaft includes a follower driven by a groove for rotating the interface.

16. The tool of claim 15 in which the tube includes a first cannula section including said groove.

17. The tool of claim 14 in which the main shaft includes a distal hook received in a slot and an opening in a proximal end of the interface shaft.

18. An intervertebral cage insertion tool system comprising:
   an intervertebral cage;
   a housing with a cannula for the intervertebral cage loadable inside the cannula;
   a shaft received in the cannula having a cage interface for engaging the intervertebral a cage loaded in the cannula;
   a linear actuator configured to advance the shaft in the cannula in a step wise fashion to advance the intervertebral cage; and
   a rotational drive configured to rotate the shaft in step wise fashion to deploy the intervertebral cage; the rotational drive includes a cam follower.

19. The tool of claim 18 in which the linear actuator includes a rack attached to the shaft and a gear mounted to the housing driving the rack to advance the shaft.

20. An intervertebral support insertion tool system comprising:
   a tube having a distal open end for insertion in a patient proximate vertebra and a proximal open end;
   a distal intervertebral support;
   a shaft received in the tube having a distal intervertebral support interface for engaging the intervertebral support loaded inside the tube; and
   means for advancing the shaft in the tube to advance the intervertebral support and for rotating the shaft in the tube to deploy the intervertebral support.

21. The tool of claim 20 in which the means for advancing the shaft in the tube and for rotating the shaft in the tube includes a rack attached to the shaft and a gear driving the rack to advance the shaft and a cam follower attached to the shaft configured to rotate the shaft.

22. The tool of claim 20 in which the tube distal end is shaped so the tube distal end can be inserted between adjacent vertebrae to distract the vertebra.

23. The tool of claim 20 in which the shaft includes a bearing between first and second sections of the shaft allowing the second section to rotate and the first section to be advanced.

24. The tool of claim 20 further including a mechanism on the housing for tensioning a wire associated with the intervertebral support.

25. The tool of claim 20 in which the shaft includes a main shaft and an interface shaft driven by the main shaft and removably attached to the intervertebral support.

26. The tool of claim 25 in which the main shaft includes a distal hook received in a slot and an opening in a proximal end of the interface shaft.

27. The tool of claim 25 in which the interface shaft includes a follower driven by a groove for rotating the interface shaft.

28. The tool of claim 27 in which the tube includes a first cannula section including said groove.

* * * * *